United States Patent
Sit et al.

(10) Patent No.: US 6,432,960 B2
(45) Date of Patent: Aug. 13, 2002

(54) SQUARATE DERIVATIVES OF DIHYDROPYRIDINE NPY ANTAGONISTS

(75) Inventors: Sing-Yuen Sit, Meriden; Graham S. Poindexter, Old Saybrook, both of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/841,349

(22) Filed: Apr. 24, 2001

Related U.S. Application Data

(60) Provisional application No. 60/203,371, filed on May 10, 2000.

(51) Int. Cl.⁷ ................. A61K 31/496; A61K 31/4545; C07D 401/12
(52) U.S. Cl. ................. 514/253.13; 514/318; 514/340; 514/356; 544/365; 546/194; 546/269.4; 546/286; 546/287; 546/318
(58) Field of Search .............. 546/194; 544/365; 514/253.13, 318

(56) References Cited

U.S. PATENT DOCUMENTS

| | | |
|---|---|---|
| 4,829,076 A | 5/1989 | Szilagyi et al. |
| 5,554,621 A | 9/1996 | Poindexter et al. |
| 5,635,503 A | 6/1997 | Poindexter et al. |
| 5,668,151 A | 9/1997 | Poindexter et al. |
| 6,001,836 A | 12/1999 | Poindexter et al. |

OTHER PUBLICATIONS

Grundemar et al, TIPS, 15, pp. 153–159, (1194).*
Gehlert et al., Exp. Opin. Invest. Drugs,6, pp. 1827–1838, (1997).*
Chaurasia, et al., "Nonpeptide Peptidomimetic Antagonists of the Neuropeptide Y Receptor: Benextramine Analogs with Selectivity for the Peripheral Y2 Receptor," J. Med. Chem., 1994, 37, 2242–2248.
Rudolf, et al., "The First Highly Potent and Selective Non–peptide Neuropeptide Y Y1 Receptor Antagonist: BIBP3226," European Journal of Pharmacology, 271, 1994, R11–R13.
Serradeil–Le Gal, et al., "SR120819A, An Orally–Active and Selective Neuropeptide Y Y1 Receptor Antagonist," FEBS Letters, 362, 1995, 192–196.

* cited by examiner

*Primary Examiner*—Emily Bernhardt
(74) *Attorney, Agent, or Firm*—Richard P. Ryan

(57) ABSTRACT

A series of antagonists of NPY have been synthesized and are comprised of squarate derivatives of 4-phenyl-1,4-dihydropyridines of Formula (I).

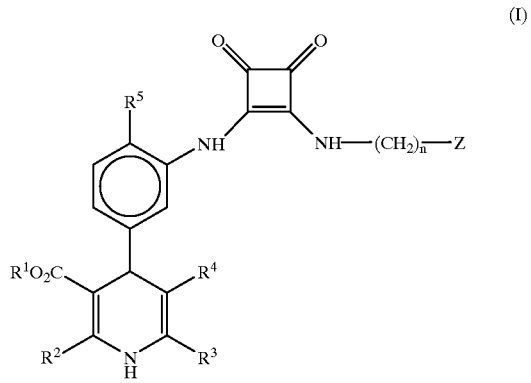

As antagonists of NPY-induced behavior, these compounds are expected to act as effective anorexiant agents in promoting weight loss and treating eating disorders.

8 Claims, No Drawings

SQUARATE DERIVATIVES OF DIHYDROPYRIDINE NPY ANTAGONISTS

CROSS REFERENCE TO RELATED APPLICATION

This non-provisional application claims priority from provisional application U.S. Ser. No. 60/203,371 filed May 10, 2000.

FIELD OF THE INVENTION

The present invention is directed to heterocyclic compounds comprising 4-phenyl-1,4-dihydropyridines having squarate moieties connected to the 3-position of the phenyl ring. More particularly, the invention is directed to NPY antagonist of squarate derivatives of 4-phenyl-1,4-dihydropyridine.

BACKGROUND OF THE INVENTION

Neuropeptide Y (NPY) is a 36 amino acid peptide first isolated in 1982 from porcine brain. The peptide is a member of a larger peptide family which also includes peptide YY (PYY), pancreatic peptide (PP), and the non-mammalian fish pancreatic peptide Y (PY). Neuropeptide Y is very highly conserved in a variety of animal, reptile and fish species. It is found in many central and peripheral sympathetic neutrons and is the most abundant peptide observed in the mammalian brain. In the brain, NPY is found most abundantly in limbic regions. The peptide has been found to elicit a number of physiological responses including appetite stimulation, anxiolysis, hypertension, and the regulation of coronary tone.

Structure-activity studies with a variety of peptide analogs (fragments, alanine replacements, point mutations, and internal deletion/cyclized derivatives) suggest a number of receptor subtypes exist for NPY. These currently include the $Y_1$, $Y_2$, $Y_3$, and the $Y_{1-like}$ or $Y_4$ subtypes.

Although a number of specific peptidic antagonists have been identified for most of the subtypes, few selective non-peptidic antagonists have been reported to date. The heterocyclic guanidine derivative He 90481 (4) was found to be a weak but competitive antagonist of NPY-induced $Ca^{++}$ entry in HEL cells ($pA_2$=4.43). The compound was also found to have $\alpha_2$-adrenergic and histaminergic activity at this dose range. D-Myo-inositol-1,2,6-triphosphate was reported to be a potent but non-competitive antagonist to NPY-induced contractions in guinea pig basilar artery. Similarly, the benextramine-like bisguanidines were reported to displace $^3$H-NPY in rat brain ($IC_{50}$, 19 and 18.4 $\mu$M) and to display functional antagonism in rat femoral artery. The bisguanidine was shown to be functionally selective for the $Y_2$ receptor since it antagonized the effect of the $NPY_2$ agonist $NPY_{13-36}$ but had no effect on the vasoconstrictive activity of the $NPY_1$ agonist [Leu$^{31}$, Pro$^{34}$] NPY as disclosed in *J. Med. Chem.*, 1994, 37, 2242-48, C. Chauraisia, et al.

Compound BIBP 3226, as reported in K. Rudolf, et al., *Eur. J. Pharmacol.*, 1994, 271, R11-R13, displaces I-125 Bolton-Hunter labeled NPY in human neuroblastoma cells (SK-N-MC). BIBP antagonized the NPY-induced increase in intracellular $Ca^{++}$ in SK-N-MC cells as well as antagonizing the NPY-induced pressor response in pithed rat experiments.

In addition to displacing I-125 labeled NPY and PYY in human neuroblastoma cells, compound SR 120819A, as reported in C. Serradeil-LeGal, et al., *FEBS Lett.*, 1995, 362,192-A6, also antagonized NPY-related increases in diastolic blood pressure in an anesthetized guinea pig model.

Over the past two decades, extensive work has been conducted relating to the 4-aryl-1,4-dihydropyridine class of compounds. Syntheses of compounds in this category have been driven by their pharmacological actions involving calcium channels rendering them useful for treating cardiovascular disorders such as ischemia and hypertension.

Numerous prior patents and publications disclose various dihydropyridine derivatives. One example is U.S. Pat. No. 4,829,076 to Szilagyi, et al. disclosing compounds of formula (1) as calcium antagonists for treating hypertension.

(1)

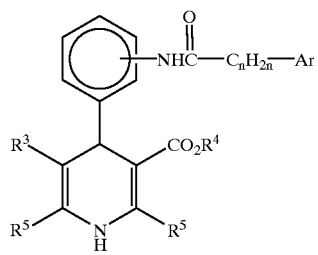

U.S. Pat. No. 5,635,503 to Poindexter, et al. discloses 4-(3-substituted-phenyl)-1,4-dihydropyridine derivatives having NPY antagonist properties. These derivatives conform to structural formula (2).

(2)

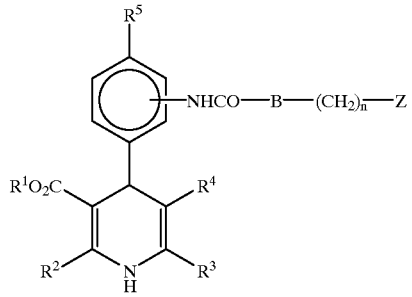

In (2), B is either a covalent bond or the group —NH—. The symbol Z denotes hetaryl moieties, examples being homopiperazinyl or piperazine.

U.S. Pat. No. 5,554,621 discloses related derivatives where Z is a fused ring or a spiro-fused nitrogen heterocyclic. U.S. Pat. No. 5,668,151 also discloses related derivatives where Z is a piperidinyl or tetrahydropyrindinyl.

U.S. Pat. No. 6,001,836 to Poindexter, et al. discloses cyanoguanidine derivatives (3) of the 4-(3-substituted-phenyl)-1,4-dihydropyridines having NPY antagonist properties.

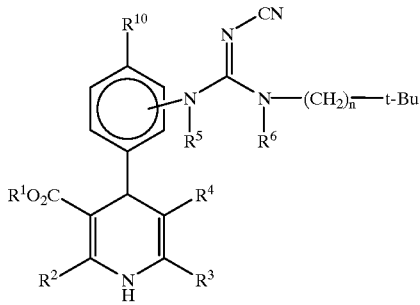

(3)

The above-noted compounds have been shown to posses antagonist activity. However, there is a continuing need for dihydropyridine derivatives having improved NPY antagonist activity.

SUMMARY OF THE INVENTION

The present invention is directed to novel dihydropyridine derivatives having NPY antagonist activity. More particularly, the invention is directed to squarate derivatives of dihydropyridines.

The compounds of the invention are effective in promoting weight loss and treating disorders in a mammal by administering to the mammal a anorexiant effective dose of an active compound of the invention.

A further aspect of the invention is to provide a method of treating clinical disorders amenable to alleviation by eliciting an $NPYY_1$ response by administering to a patient an effective amount of a compound of the invention.

Another aspect of the invention is to provide a pharmaceutical composition for use in promoting weight loss and treating eating disorders, where the composition comprises an anorexiant effective amount of an active compound of the invention and a pharmaceutically acceptable carrier.

The compounds of the invention have the Formula I and its pharmaceutically acceptable acid addition salts or hydrates thereof

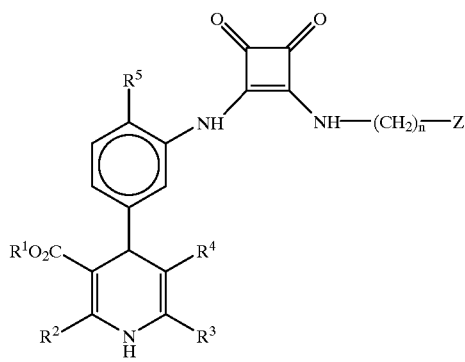

(I)

wherein $R^1$ is lower alkyl;

$R^2$ and $R^3$ are independently selected from cyano and lower alkyl;

$R^4$ is selected from $-CO_2R^1$, cyano and

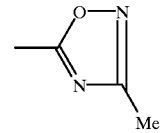

$R^5$ is selected from hydrogen, halogen, hydroxy, lower alkyl, lower alkenyloxy, and lower alkoxy;

n is an integer selected from 2 to 5;

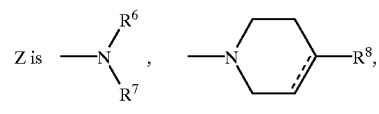

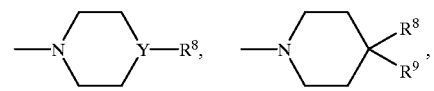

in which Y is $-CH-$ or N, $R^6$ and $R^7$ are independently selected from lower alkyl and lower alkanol; the solid and broken line denote a single or double covalent bond; $R^9$ is selected from hydrogen, hydroxy and cyano; $R^8$ is selected from hydrogen, lower alkyl, $-CO_2R^1$, $-(CH_2)_mX$, and $-(CH_2)_nNR^{10}R^{11}$, wherein m is zero or an integer from 1 to 3 and X is $C_{3-7}$ cycloalkyl, naphthyl, and

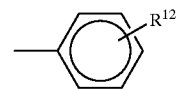

with $R^{12}$ being lower alkyl, lower alkenyl, lower alkoxy, hydrogen, halogen, hydroxy and dialkylamino, and $R^{10}$ and $R^{11}$ are lower alkyl or are taken together as a $C_{3-5}$ alkylene chain or an ethyl-oxy-ethyl chain.

These and other aspects of the invention will become apparent to one skilled in the art as described in the following detailed description.

DETAILED DESCRIPTION OF THE INVENTION

The present invention is directed to novel compounds having $NPYY_1$, antagonist activity and pharmaceutical compositions containing the novel compounds. The invention is further directed to a method of treating clinical disorders, such as eating disorders, using the novel compounds of the invention.

The compounds of the invention have the Formula I

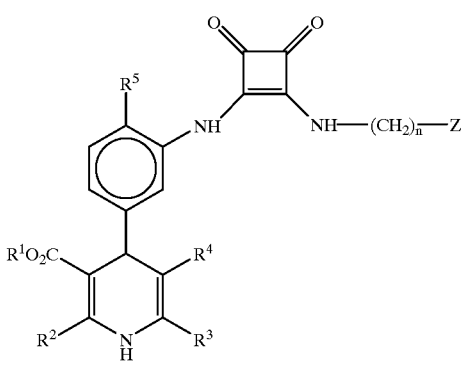

(I)

The compounds within the preview of the invention include the pharmaceutically acceptable acid addition salts and/or hydrates of the compounds of Formula I.

In the Formula I, $R^1$ is lower alkyl; $R^2$ and $R^3$ are independently selected from cyano and lower alkyl;

$R^4$ is selected from —$CO_2R^1$, cyano and

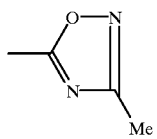

$R^5$ is selected from hydrogen, halogen, hydroxy, lower alkyl, lower alkenyloxy, and lower alkoxy;
n is an integer selected from 2 to 5;

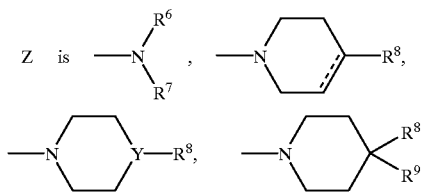

in which Y is —CH— or N, $R^6$ and $R^7$ are independently selected from lower alkyl and lower alkanol; the solid and broken line denote a single or double covalent bond; $R^9$ is selected from hydrogen, hydroxy and cyano; $R^8$ is selected from hydrogen, lower alkyl, —$CO_2R^1$, —$(CH_2)_mX$, and —$(CH_2)_nNR^{10}R^{11}$, wherein m is zero or an integer from 1 to 3 and X is $C_{3-7}$ cycloalkyl, naphthyl, and

with $R^{12}$ being lower alkyl, lower alkenyl, lower alkoxy, hydrogen, halogen, hydroxy and dialkylamino, and $R^{10}$ and $R^{11}$ are lower alkyl or are taken together as a $C_{3-5}$ alkylene chain or an ethyl-oxy-ethyl chain.

The term "lower" refers to substituents such as alkyl or alkoxy groups that contain from one to four carbon atoms. Alkenyl groups generally contain two to four carbon atoms.

In embodiments of the invention, $R^1$ preferably is methyl. $R^2$ and $R^3$ are preferably methyl. $R^5$ is preferably hydrogen or fluorine. Z is preferably an alkyl amine. In one preferred embodiment of the invention, Z is 4-(3-methoxyphenyl)-1-piperidinyl or 4-cyclohexyl-1-piperazinyl.

The compounds of the present invention can exist as optical isomers and both the racemic mixtures of these isomers as well as the individual optical isomers themselves are within the scope of the present invention. The racemic mixtures can be separated into their individual isomers through well-known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, dichloroacetic acid, tartaric acid, lactic acid, succinic acid, citric acid, maleic acid, fumaric acid, sorbic acid, aconitic acid, salicyclic acid, phthalic acid, enanthic acid, and the like.

The compounds of the invention can be synthesized by various processes. One such process is outlined below where the aniline of Formula (II) is reacted with 3,4-diethoxy-3-cyclobutene-1,2-dione under reflux conditions in dimethylformamide (DMF) or ethanol to yield the intermediates of Formula (III). The intermediates (III) are subsequently condensed with propanamines (IV) to produce the corresponding squarate derivatives.

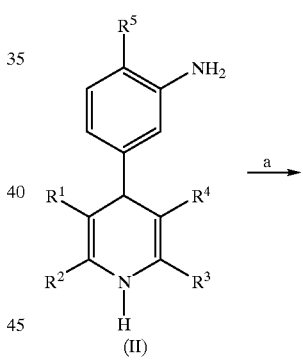

(II)

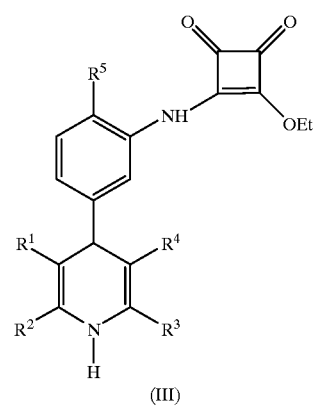

(III)

a 3,4-diethoxy-3-cyclobutene-1,2-dione reflux in DMF or ethanol

In one preferred embodiment, the compounds of the invention have

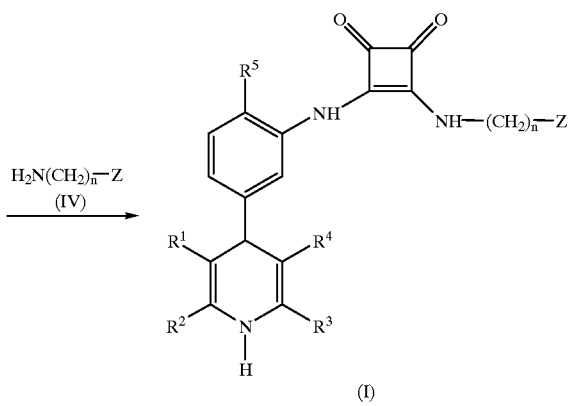

the structure of Formula IA below

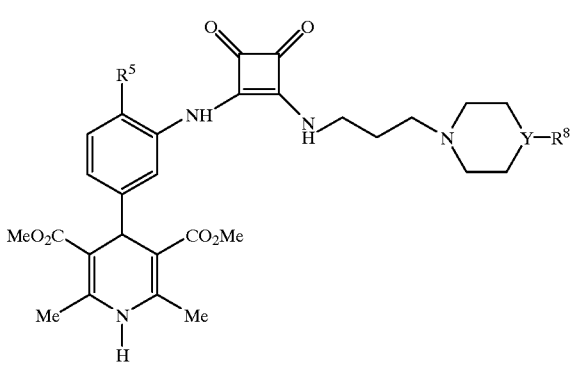

where $R^5$ is hydrogen or fluorine, Y is CH or N and $R^8$ is 3-methoxyphenyl or cyclohexyl.

The compounds of the invention demonstrate binding affinity at NPY $Y_1$ receptors. This pharmacologic activity is assayed in SK-N-MC (human neuroblastoma) cell membranes using iodine-125-labeled I-PYY as a radioligand. The compounds of Formula I had good binding affinities as evidenced by $IC_{50}$ values being about 10 µM or less at NPY $Y_1$ receptors. Preferred compounds have $IC_{50}$ values less than 100 nM and most preferred compounds have $IC_{50}$ values of less than 10 nM. These types of dihydropyridines have significant affinity for $\alpha_1$-adrenergic receptors and/or $Ca^{++}$ channels.

Pharmacologically, the compounds of Formula I act as selective NPY antagonists at NPY $Y_1$ receptor sites. As such, the compounds of Formula I are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale. These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrhythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal track;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and reproductive disorders such as benign prostatic hyperplasia and male erectile dysfunction;

conditions or disorders associated with inflammation;

respiratory diseases, such as asthma and conditions related to asthma and bronchoconstriction;

diseases related to abnormal hormone release, such as leutinizing hormone, growth hormone, insulin and prolactin; and sleep disturbance and diabetes.

There is evidence that NPY contributes to certain symptoms in these disorders, such as, hypertension, eating disorders, and depression/anxiety, as well as circadian rhythms. Compounds of this invention are expected to be useful in treating these disorders as well as sleep disturbance and diabetes.

Selected compounds are tested further for their ability to block or stimulate NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula I compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 50 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat the various diseases, conditions, and disorders listed above.

Therapeutically, the compounds of Formula I are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier. The carrier comprises one or more solid, semi-solid, or liquid diluent, filler, and formulation adjuvant that is non-toxic, inert and pharmaceutically acceptable.

Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the predetermined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate).

Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethylene glycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF SPECIFIC EXAMPLES

The following examples set forth the process for producing various squarate derivatives of the dihydropyridine. The binding affinities were determined at NPY $Y_1$ receptors. The pharmacologic activity was assayed in SK-N-MC (human neuroblastoma) cell membranes using iodine-125-labeled 1-PYY as ratio ligand. Examples 1 and 2 are directed to the production of the intermediates. Examples 3–6 are directed to the process of producing the squarate derivatives. Table 1 shows the binding affinity for the intermediates of Examples 1 and 2, and the binding affinity of the resulting compounds of Examples 3–6.

While many of the synthetic intermediates and starting compounds may be commercially available, they are also described in previous patents directed to the dihydropyridine series of NPY antagonists such as U.S. Pat. No. 5,668,151 and U.S. Pat. No. 6,001,836 which are incorporated in their entirety herein.

The compounds which constitute this invention and their methods of preparation will appear more fully from a consideration of the following examples which are given for the purpose of illustration only and are not to be construed as limiting the invention in sphere or scope. All temperatures are understood to be in degrees C. when not specified.

The nuclear magnetic resonance ($^1$H and $^{13}$C NMR) spectral characteristics refer to chemical shifts ($\delta$) expressed in parts per million (ppm) versus tetramethylsilane (TMS) as reference standard). The relative area reported for the various shifts in the proton NMR spectral data corresponds to the number of hydrogen atoms of a particular functional type of molecule. The nature of the shits as to multiplicity is reported as broad single (br s), multiplet (m), doublet (d), triplet (t), doublets of doublets (dd), quartet (q) or pentuplet (p). Abbreviations employed as DMSO-$d_6$, (deuterodimethyl-sulfoxide), CDCl$_3$ (deuterochloroform), and are otherwise conventional. The infrared (IR) spectral descriptions include only absorption wave numbers (cm$^{-1}$) having functional group identification value. The IR determinations were generally employed using potassium bromide (KBr) as diluent. The elemental analyses are reported as percent by weight. Melting points were obtained using a Thomas Hoover capillary apparatus and are uncorrected. Mass spectra (m/z; MH$^+$) and analytic HPLC (retention time and peak area %) data were obtained.

Example 1

4-[3-[(2-Ethoxy-3,4-dioxo-1-cyclobuten-1-yl)amino] phenyl]-1,4-dihydro-2,6-dimethyl-3,5-pyridinedicarboxylic Acid, Dimethyl Ester A mixture of the starting aniline 3-amino-1,4-dihydro-2, 6-dimethyl-3,5-pyridinedicarboxylic acid, dimethyl ester (950 mg, 3.01 mmol) and 3,4-diethoxy-3-cyclobutene-1,2-dione (526.5 mg, 3.09 mmol) in 6 mL of dry dimethylformamide (DMF) under nitrogen atmosphere was heated to 100° C. for 16 hours. Water was added into the crude reaction mixture and the organic materials were extracted into ethyl acetate (3×15 mL). The desired product (690 mg, 52.1%) separated out upon concentration under reduced pressure as an off-white crystalline solid: mp 249-252° C.; $^1$H NMR (DMSO-$d_6$) $\delta$ 10.66 (br. s, 1H), 8.92 (br. s, 1H), 7.19 (m, 3H), 6.89 (m, 1H), 4.89 (s, 1H), 4.75 (q, 2H, J=7.1 Hz), 3.55 (s, 6H), 2.27 (s, 6H), 1.41 (t, 3H, J=7.1 Hz), $^{13}$C NMR (DMSO-$d_6$) $\delta$ 196.88, 184.17, 167.17, 148.73, 145.87, 137.70, 128.42, 122.68, 118.12, 117.11, 100.88, 69.30, 50.54, 18.10, 15.51. Anal Calcd for $C_{23}H_{24}N_2O_7 \cdot 0.4 H_2O$: C, 61.71; H, 5.58; N, 6.26. Found: C, 61.74; H, 5.48; N, 6.37.

Example 2

4-[3-[(2-Ethoxy-3,4-dioxo-1cyclobuten-1-yl)amino]-4-fluorophenyl]-1,4-dihydro-2,6-dimethyl-3,5-pyridinedicarboxylic Acid, Dimethyl Ester A mixture of the starting aniline 3-amino-4-fluoro-1,4-dihydro-2,6-dimethyl-3,5-pyridinedicarboxylic acid, dimethyl ester (1.03 g, 3.08 mmol) and 3,4-diethoxy-3-cyclobutene-1,2-dione (632.5 mg, 3.72 mmol) in 1 mL of absolute ethanol under nitrogen atmosphere was refluxed for 16 hours. Thin layer chromatography (TLC) eluted 5 times with 1:1 v/v ethylacetate/hexanes mixture revealed two new products at Rf=0.05 and 0.5. Water was added into the crude reaction mixture and the organic materials were extracted into ethyl acetate (15 mL×3). The desired product (580 mg, 41.1%, less polar component), and the dimeric side product (460 mg, 40.0%, more polar component) were separated by $SiO_2$ column chromatography eluted with pure hexanes, followed by 5% ethyl acetate in hexanes: mp 203–205° C.; $^1$H NMR (DMSO-$d_6$) δ 10.57 (br. s, 1 H), 8.95 (br. s, 1H), 7.11 (m, 2H), 6.97 (m, 1H), 4.86 (s, 1H), 4.67 (q, 2H, J=7.1 Hz), 3.55 (s, 6H), 2.25 (s, 6H), 1.36 (t, 3H, J=7.1 Hz), $^{13}$C NMR (DMSO-$d_6$) δ 184.35, 170.80, 167.21, 146.16, 124.63, 123.40, 100.95, 69.31, 50.72, 18.25, 15.57. Anal Calcd. for $C_{23}H_{23}FN_2O_7$•0.12 $H_2O$: C, 59.98; H, 5.09; N, 6.08. Found: C, 59.99; H, 5.21; N, 5.95.

Example 3

1,4-Dihydro-4-[3-[[2-[[3-[4-(3-methoxyphenyl)-1-piperidinyl]propyl]amino]-3,4-dioxo-1-cyclobuten-1-yl]amino]phenyl]-2,3-dimethyl-3,5-pyridinedicarboxylic Acid, Dimethyl Ester The compound of Example 1 (54.7 mg, 0.124 mmol) and 4-(3-methoxyphenyl)piperidine-1-propanamine (41 mg, 0.165 mmol) were heated together in 2 mL DMF at 100° C. for 16 hours. Water was added into this crude reaction mixture after it was cooled to room temperature and the organic material was extracted with ethyl acetate (3×15 mL). Thin layer chromatography on $SiO_2$ eluted with 10% methanol in methylene chloride showed essentially one single spot. This material was allowed to pass through a short bed of silica gel (Merck Type-H) and the pure product was, recovered as a foam after removal of solvents (43 mg, 54.0%). $^1$H NMR (DMSO-$d_6$) δ 9.86 (br. s, 1H), 8.93 (br. s, 1H), 7.95 (br. s, 1H), 7.30 (d, 1H, J=7.7 Hz), 7.16 (m, 4H), 6.79 (m, 4H), 4.88 (s, 1H), 3.72 (s, 3H), 3.65 (m, 2H), 3.55 (s, 6H), 3.06 (m, 2H), 2.5 (m, 2H), 2.26 (s, 6H), 1.8 (m, 8H), $^{13}$C NMR (DMSO-$d_6$) δ 167.38, 159.31, 145.95, 138.97, 129.36, 118.78, 112.45, 101.08, 54.87, 50.67, 18.28. Anal Calcd. for $C_{36}H_{42}N_4O_7$•2.10 $H_2O$: C, 63.53; H, 6.84; N, 8.23. Found: C, 63.48; H, 6.85; N, 8.58.

Example 4

4-[4-Fluoro-3-[[2-[[3-[4-(3-methoxyphenyl)-1-piperidinyl]propyl]amino]-3,4-dioxo-1-cyclobuten-1-yl]amino]phenyl]-1,4-dihydro-2,6-dimethyl-3,5-pyridinedicarboxylic Acid, Dimethyl Ester The compound of Example 2 (98.3 mg, 0.215 mmol) and 4-(3-methoxyphenyl)piperidine-1-propanamine (64 mg, 0.258 mmol) were stirred in 2 mL DMF at room temperature for 64 hours. The crude reaction mixture was evaporated to dryness under high vacuum (0.1 mmHg) at 50–55° C. The resulting gum was triturated with methylene chloride followed by the addition of hexanes. The titled compound precipitated out as fine creamy white crystalline solid (120 mg, 84.6%): mp 205–207° C.; $^1$H NMR (DMSO-$d_6$) δ 9.38 (br. s, 1H), 8.96 (br. s, 1H), 8.04 (br. t, 1H, J=3 Hz), 7.80 (d, 1H, J=7.2 Hz), 7.10 (m, 2H), 6.77 (m, 4H), 4.85 (s, 1H), 3.71 (s, 3H), 3.65 (q, 2H, J=6.0 Hz), 3.53 (s, 6H), 2.95 (d, 2H, J=10.5 Hz), 2.40 (m, 3H), 2.25 (s, 6H), 1.97 (m, 2H), 1.67.(m, 6H), $^{13}$C NMR (DMSO-$d_6$) δ 184.94, 179.65, 169.52, 167.32, 163.03, 159.26, 147.95, 146.23, 145.07, 129.25, 126.76, 126.62, 119.68, 118.81, 114.66, 114.40, 112.41, 111.35, 100.93, 55.14, 54.83, 53.73, 50.60, 32.93, 27.84, 18.31. Anal Calcd. for $C_{36}H_{41}FN_4O_7$•0.14 $H_2O$: C, 65.19; H, 6.27; N, 8.45. Found: C, 65.20; H, 6.28; N, 8.37.

Example 5

4-[3-[[2-[[3-(4-cyclohexyl-1-piperazinyl)propyl]amino]-3,4-dioxo-1-cyclobuten-1-yl]amino]phenyl]-1,4-dihydro-2,6-dimethyl-3,5-pyridinedicarboxylic Acid, Dimethyl Ester The compound of Example 1 (160 mg, 0.364 mmol) and 4-cyclohexyl-1-piperazine-1-propanamine (81.4 mg, 0.362 mmol) were stirred in 2 mL DMF at room temperature for 64 hours. The crude reaction mixture was evaporated to dryness under high vacuum (0.1 mmHg) at 50–55° C. The resulting gum was triturated with methylene chloride followed by the addition of hexanes. The titled compound precipitated out as fine creamy white crystalline solid (165 mg, 73.6%): mp 210–212° C.; $^1$H NMR (DMSO-$d_6$) δ 9.52 (br. s, 1H), 8.91 (br. s, 1H), 7.54 (br. 1H), 7.27 (d, 1H, J=7.3 Hz), 7.16 (m, 2H), 6.80 (d, 1H, J=7.5 Hz), 4.88 (s, 1H), 3.61 (m, 2H), 3.55 (s, 6H), 2.45 (m, 5H), 2.30 (m, 4H), 2.26 (s, 6H), 1.69 (m, 7H), 1.53 (br. d, 1H, J=11.0 Hz), 1.11 (m, 6H); $^{13}$C NMR (DMSO-$d_6$) δ 207.50, 207.28, 206.89, 203.73, 199.89, 194.77, 193.47, 192.12, 169.21, 167.38, 163.58, 153.67, 149.15, 145.92, 138.90, 128.87, 121.51, 116.60, 115.86, 101.11, 62.50, 54.94, 53.29, 50.57, 49.90, 48.28, 42.22, 28.32, 27.73, 26.26, 23.50, 18.29, 17.37. Anal Calcd. for $C_{34}H_{45}N_5O_6$•0.13 $H_2O$: C, 65.64; H, 7.33; N, 11.26. Found: C, 65.65; H, 7.25; N, 11.09.

Example 6

4-[3-[[2-[[3-(4-cyclohexyl-1-piperazinyl)propyl]amino]-3,4-dioxo-1-cyclobuten-1-yl]amino]-4-fluorophenyl]-1,4-dihydro-2,6-dimethyl-3,5-pyridinedicarboxylic Acid, Dimethyl Ester The compound of Example 2 (147 mg, 0.321 mmol) and 4-cyclohexyl-1-piperazine-1-propanamine (72 mg, 0.320 mmol) were stirred in 2 mL DMF at room temperature for 64 hours. The crude reaction mixture was evaporated to dryness under high vacuum (0.1 mmHg) at 50–55° C. The resulting gum was triturated with methylene chloride followed by the addition of hexanes. The titled compound precipitated out as fine creamy white crystalline solid (158 mg, 77.5%): mp 229-230° C.; $^1$H NMR (DMSO-$d_6$) δ 9.37 (br. s, 1H), 8.96 (br. s, 1H), 8.03 (br. 1H), 7.79 (d, 1H, J=7.6 Hz), 7.59 (dd, 1H, J=8.98, 5.21 Hz), 7.07 (dd, 1H, J=8.46, 11.37 Hz), 6.2 (m, 1H), 4.84 (s, 1H), 3.62–3.60 (m, 2H), 3.54 (s, 6H), 2.45 (m, 5H), 2.33-2.26 (m, 4H), 2.26 (s, 6H), 1.70–1.68 (m, 7H), 1.59-1.52 (br. 1H), 1.18-1.04 (m, 6H), $^{13}$C NMR (DMSO-$d_6$) δ 179.63, 169.50, 167.31, 146.22, 129.07, 126.75, 125.98, 122.13, 119.68, 100.93, 62.55, 54.87, 50.60, 48.22, 42.13, 28.20, 27.62, 25.86, 25.57, 25.21, 18.31. Anal Calcd. for $C_{34}H_{44}FN_5O_6$•0.05 $H_2O$: C, 63.94; H, 6.96; N, 10.97. Found: C, 63.95; H, 6.94; N, 10.74.

Example 7

The compounds of Examples 1–6 were tested for binding affinity at NPY $Y_1$ receptors. The pharmacologic activity was assayed in SK-N-MC (human neuroplastoma) cell membranes using iodine-125 labeled I-PYY as a radioligand. The results are set forth in Table 1 below.

TABLE 1

| Compound | NPY $Y_1$ (nM) |
|---|---|
| Example 1 | >1000 nM |
| Example 2 | >1000 nM |
| Example 3 | 24.6 |
| Example 4 | 65.8 |
| Example 5 | 140 |
| Example 6 | 950 |

What is claimed is:

1. A compound of Formula I and its pharmaceutically acceptable acid addition salts or hydrates thereof

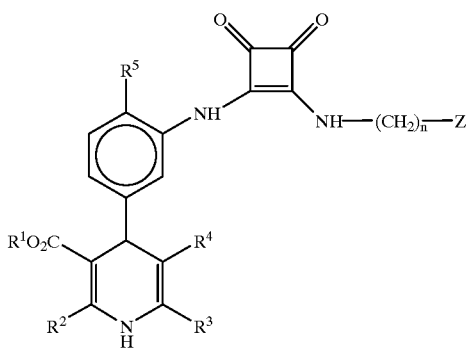

(I)

wherein
  $R^1$ is lower alkyl;
  $R^2$ and $R^3$ are independently selected from cyano and lower alkyl;
  $R^4$ is selected from —$CO_2R^1$, cyano and

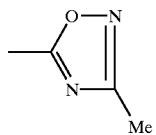

$R^5$ is selected from hydrogen, halogen, hydroxy, lower alkyl, lower alkenyloxy, and lower alkoxy;
  n is an integer selected from 2 to 5;

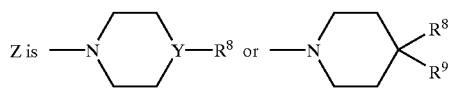

in which Y is —CH— or N; $R^9$ is selected from hydrogen, hydroxy and cyano; and $R^8$ is selected from hydrogen, lower alkyl, —$CO_2R^1$, —$(CH_2)_mX$, and —$(CH_2)_nNR^{10}R^{11}$,
  wherein m is zero or an integer from 1 to 3 and X is $C_{3-7}$ cycloalkyl, naphthyl, and

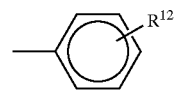

with $R^{12}$ being lower alkyl, lower alkenyl, lower alkoxy, hydrogen, halogen, hydroxy and dialkylamino, and $R^{10}$ and $R^{11}$ are lower alkyl or are taken together as a $C_{3-5}$ alkylene chain or an ethyl-oxy-ethyl chain.

2. A compound of claim 1 wherein Z is

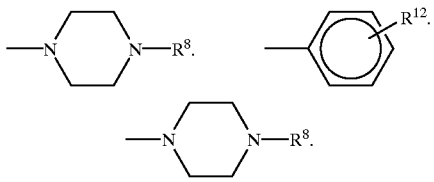

3. A compound of claim 1 wherein $R^8$ is

4. A compound of claim 3 wherein $R^8$ is methoxy.
5. A compound of claim 1 wherein $R^8$ is cyclohexyl.
6. A compound of claim 1 selected from the group consisting of
  1,4-dihydro-4-[3-[[2-[[3-[4-(3-methoxyphenyl)-1-piperidinyl]propyl]amino]-3,4-dioxo-1-cyclobuten-1-yl]amino]phenyl]-2,3-dimethyl-3,5-pyridinedicarboxylic acid, dimethyl ester,
  4-[4-Fluoro-3-[[2-[[3-[4-(3-methoxyphenyl)-1-piperidinyl]propyl]amino]-3,4-dioxo-1-cyclobuten-1-yl]amino]phenyl]-1,4-dihydro-2,6-dimethyl-3,5-pyridinedicarboxylic acid, dimethyl ester,
  4-[3-[[2-[[3-(4-cyclohexyl-1-piperazinyl)propyl]amino]-3,4-dioxo-1-cyclobuten-1-yl]amino]phenyl]-1,4-dihydro-2,6-dimethyl-3,5-pyridinedicarboxylic acid, dimethyl ester, and
  4-[3-[[2-[[3-(4-cyclohexyl-1-piperazinyl)propyl]amino]-3,4-dioxo-1-cyclobuten-1-yl]amino]-4-fluorophenyl]-1,4-dihydro-2,6-dimethyl-3,5-pyridinedicarboxylic acid, dimethyl ester.

7. A method of promoting weight loss and treating eating disorders in a mammal comprising administering to a mammalian host an anorexiant effective dose of a compound claimed in claim 1.

8. A pharmaceutical composition for use in promoting weight loss and treating eating disorders, the composition comprising an anorexiant effective amount of a compound claimed in claim 1 in combination with a pharmaceutically acceptable carrier.

* * * * *